Figure 1:
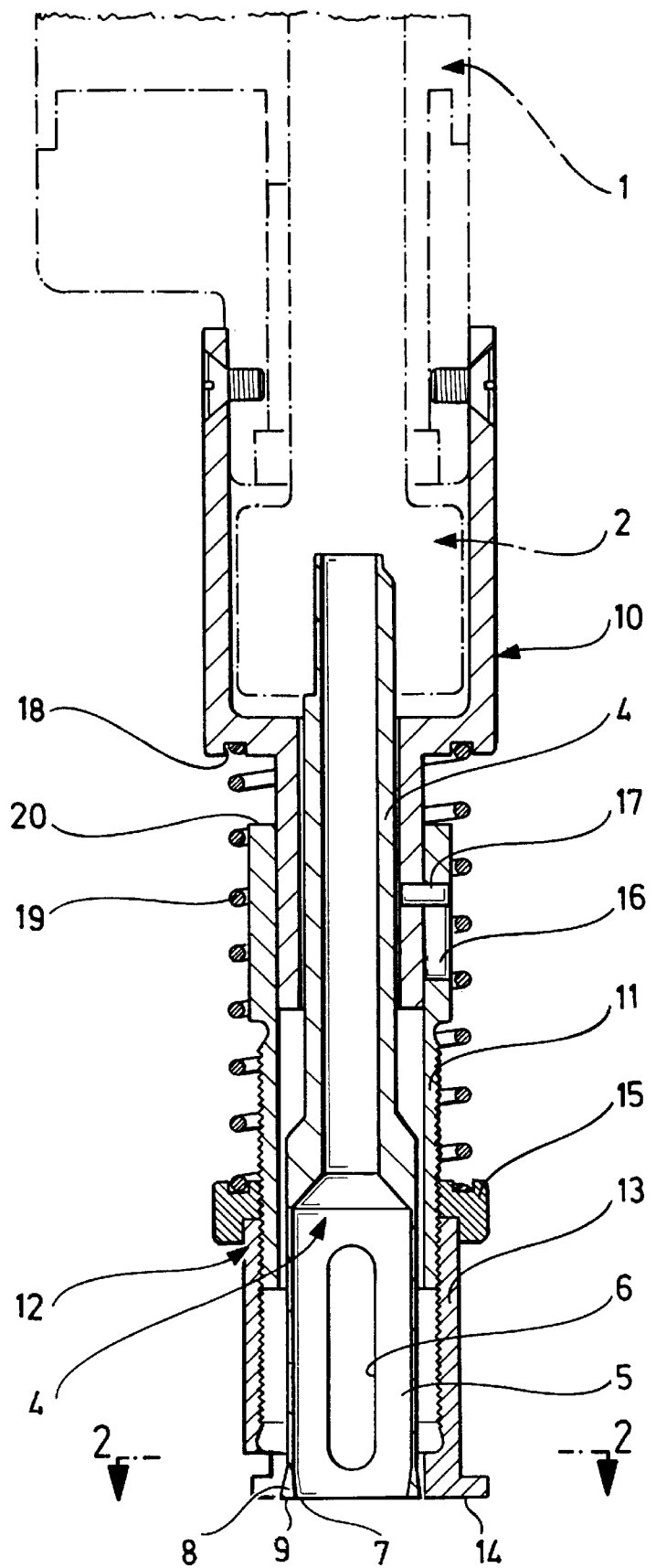

United States Patent
Haeusler et al.

[11] Patent Number: 6,129,731
[45] Date of Patent: Oct. 10, 2000

[54] SURGICAL INSTRUMENT FOR CUTTING-OUT A CRANIAL DISC FROM THE CRANIAL BONE

[75] Inventors: Rainer Haeusler; Roland Alois Hoegerle, both of Tuttlingen; Theodor Lutze, Balgheim; Norbert Mattes, Muhlheim, all of Germany

[73] Assignee: Aesculap AG & Co. KG, Tuttlingen, Germany

[21] Appl. No.: 09/159,922

[22] Filed: Sep. 24, 1998

[51] Int. Cl.$^7$ .................................................. A61B 17/32
[52] U.S. Cl. ............................ 606/79; 606/178; 606/179; 606/180
[58] Field of Search .................................. 606/79, 80, 83, 606/167, 171, 179, 180, 178

[56] References Cited

U.S. PATENT DOCUMENTS

| | | | |
|---|---|---|---|
| 2,525,669 | 10/1950 | Hainault | 606/80 |
| 4,362,161 | 12/1982 | Reimels et al. | 606/80 |
| 5,197,967 | 3/1993 | Wilson | 606/79 |

FOREIGN PATENT DOCUMENTS

| | | |
|---|---|---|
| 36 24 860 | 4/1987 | Germany . |
| 88 06 721 | 8/1988 | Germany . |

*Primary Examiner*—Michael Buiz
*Assistant Examiner*—Julian W. Woo
*Attorney, Agent, or Firm*—Barry R. Lipsitz

[57] ABSTRACT

A surgical instrument is provided for cutting a cranial disc from a skull cap. A cylindrical trepanning cutter is provided with teeth on its frontal edge. The teeth cut in both peripheral directions. A driving means drives the trepanning cutter with a periodically altering direction of rotation through an angle of rotation of substantially less than 360°. The angle is at least large enough for the teeth to be displaced by one tooth spacing along the frontal edge of the cylindrical trepanning cutter.

17 Claims, 2 Drawing Sheets

SURGICAL INSTRUMENT FOR CUTTING-OUT A CRANIAL DISC FROM THE CRANIAL BONE

The invention relates to a surgical instrument for cutting-out a cranial disc from the skull cap.

For the purposes of gaining access to the interior of the skull, it is known to remove bone material in a break-through or access region by means of a grinding process using suitable cutters, this being effected using so-called trepans. These are of course very easy to use but have the disadvantage that the bone material is destroyed in the area of the opening.

It is also known to cut-out disc shaped regions of the skull cap with the help of saw-type instruments or with the help of pin-hole or wire saws. However, a pre-requisite for processes of this kind is the provision of bore holes and the processes themselves are complicated and, in addition, a considerable portion of the bone material is also removed when using such a process.

The object of the invention is to design a surgical instrument in accordance with the first part of claim 1, which, on the one hand, is easy to use and, on the other, one which causes as little damage as possible to the bone material in the access region. In addition, any danger of injury should be minimised insofar as possible.

In accordance with the invention, this object is achieved by a surgical instrument for cutting-out a cranial disc from the skull cap which is characterised by a cylindrical trepanning cutter or drill provided with teeth on its frontal edge which said teeth cut in both peripheral directions, and by a driving means which drives the trepanning cutter with a periodically altering direction of rotation through an angle of rotation of substantially less than 360° but which said angle is at least large enough for the teeth to be thereby displaced by one tooth spacing along the frontal edge.

By using such an oscillating trepanning cutter, one can saw-out a circular cranial disc from the skull cap whereby the oscillating movement of the trepanning cutter, which is effected over only a relatively small peripheral angle, has various operational advantages. Thus, it is very easy to place such an oscillating trepanning cutter at the wanted position and, when necessary, it is even possible to arrange several circular access points adjacent to one another or even such that they overlap without any fear of the trepanning cutter deviating from the position in which it was placed when starting-up the trepanning cutter.

When using this instrument, it is also possible to interrupt the boring or drilling process at any time and then, following the interruption, to replace the trepanning cutter into the partially produced circular incision and then carry on with the boring action. A very special and substantial advantage lies in that, following the piercing of the skull cap and in the possible event that the teeth come into contact with the dura located below the skull cap, any danger of injury to the soft tissue i.e. the dura and the grey matter, can, to a large extent, be avoided. Whilst the hard bone material is abraded away by the oscillating teeth, the soft tissue is able to follow the relatively small sweeping movement of the teeth without being damaged thereby. Thus, both the dura and the grey matter may possibly be moved in oscillatory manner by the teeth but the soft tissues can withstand such movement without any damage.

By virtue of achieving access to the interior of the skull in the manner described, the bone material is only damaged to a minimum extent, that is to say, that abrasion only occurs in the extremely small cutting region of the trepanning cutter. An undamaged cranial disc is obtained in the central region of the passage created and this can be replaced in the opening after the operation has ended and then fixed in place therein.

In accordance with a particularly preferred embodiment of the invention, there is associated with the trepanning cutter a support means which is displaceable along the rotational axis of the trepanning cutter between a starting position in which the support means projects beyond the frontal edge and an end position in which it liberates or exposes the frontal edge and a section of the trepanning cutter abutting thereon. This support means helps the operator to position the trepanning cutter perpendicularly relative to the surface of the skull and to hold it in this position during the boring process. It is particularly expedient thereby, if the support means is moved into the starting position by means of a spring. The boring process is thereby effected against the force of this spring since the trepanning cutter moves into the cranial bone during the boring process and thereby displaces the support means against the action of the spring. This restraining force becomes increasingly large and thus, above all, ensures that the operator will not penetrate the grey matter unintentionally with the trepanning cutter when breaking through the cutting location.

This may be additionally assured by means of a stop which limits the displacement path of the support means at the end position so guaranteeing a maximum penetration depth for the trepanning cutter.

It is expedient if the stop is adjustable in a direction along the displacement path of the support means. It is then possible for the operator to adjust the maximum penetration depth in dependence on the prevailing circumstances.

In a first preferred embodiment, provision is made for the support means to surround the trepanning cutter externally.

In particular, provision may be made for the support means to comprise a plurality of mutually circumferentially displaced support feet, in the form of a tripod for example.

Between the support feet, there is thus provided an open break-through area via which, on the one hand, the cut bone material can emerge while, on the other, it is ensured that the cutting location is fully visible.

The support feet may, for example, be mounted on a common carrier means that is displaceable in parallel with the rotational axis of the trepanning cutter, it then being advantageous if the stop limiting the displacement path of the support is mounted on this carrier means.

In particular, the carrier means is in the form of a ring which is screwed onto a thread on the stop which itself is in the form of a sleeve. In addition, the effective length of the stop and hence the desired penetration depth of the trepanning cutter can be adjusted by means of this screwing action.

A helical spring supported on the ring may surround the sleeve externally.

In this case, the sleeve preferably forms a longitudinal guide means for the movement of the support.

Basically, it is also possible for the support means to be disposed internally of the trepanning cutter, for example, the support means may embrace a spring-loaded die which is insertable into the trepanning cutter.

Normally, either an external or an internal support is sufficient but it is equally possible to provide both types of support at the same time.

It is also expedient if the trepanning cutter comprises openings in that wall thereof which abuts onto the frontal edge. These window-like openings allow bone material to be ejected and also make it possible for the incision point to be seen in this region.

It is particularly advantageous if the teeth on the exterior surface of the trepanning cutter and/or on the interior surface of the trepanning cutter widen out radially towards the frontal edge. The teeth thus have an open section. The temperature development resulting from the cutting process can thereby be minimised so that damage to the tissue caused by temperature effects will be avoided. Moreover, this type of toothing leads to there being a residue of bone in front of the shears on the teeth thus producing an additional protective separation of the trepanning cutter from the soft tissue located below the skull cap.

Figure 2:
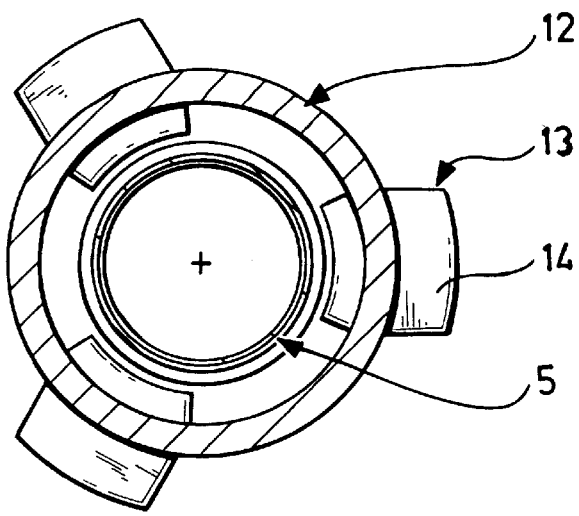

The following description of preferred embodiments of the invention in combination with the drawing will serve to provide a more detailed explanation. Therein:

FIG. 1 shows a longitudinal sectional view through the front portion of a surgical instrument including an oscillating trepanning cutter and an external support means;

FIG. 2 a sectional view along the line 2—2 in FIG. 1 and

Figure 3:
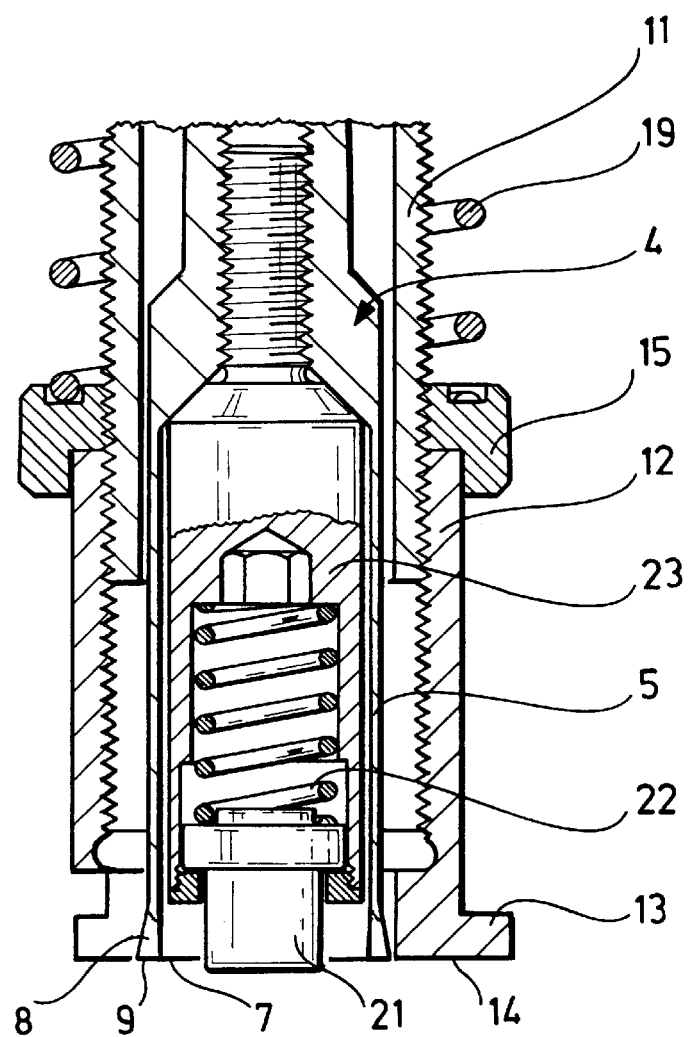

FIG. 3 a view similar to FIG. 1 in the case of a trepanning cutter having internal and external support means.

The instrument illustrated in the drawing is placed on a conventional drive appliance 1 comprising an electric motor which is not illustrated in the drawing and which sets a chuck 2 into rotation about its longitudinal axis, namely, into a rotational mode wherein the direction of rotation periodically alters and is merely effected through a relatively small angular range, for example, an angular range of between 1° and 30°, preferably 3° and 12°.

The chuck 2 accommodates the shaft 3 of a trepanning cutter 4 in an interlocking plug-type coupling, said trepanning cutter widening towards its free end into the form of a cylindrical sleeve 5 whose walls incorporate sideways window-like openings 6 and the frontal edge 7 of which is provided with a plurality of teeth 8. These teeth 8 are distributed uniformly over the frontal edge 7 and carry cutting edges or shears 9 on both side so that the teeth will cut in both directions of rotation when they are applied to bony tissue.

The teeth widen out towards the frontal edge 7, both on the outside and on the inside, so that they are widened in the region of the cutting edges 9 relative to the thickness of the wall of the sleeve 5 (FIGS. 1 and 3).

The chuck 2 and the part of the shaft 3 of the trepanning cutter 4 on the chuck side are surrounded by a stepped, sleeve-shaped housing 10 which is mounted on the drive appliance 1. A sleeve 11 having an external thread is mounted on this housing 10 in longitudinally displaceable manner and an annular carrier member 12 is screwed onto the sleeve 11, said carrier member having downwardly projecting support feet 13 that extend in parallel with the rotational axis of the trepanning cutter 4. In the embodiment of FIG. 1, three support feet are arranged on the carrier member 12, these being angularly displaced relative to one another around the periphery by 120°. The support feet 13 end in a support surface 14 which extends in a radial direction perpendicularly to the rotational axis of the trepanning cutter 4.

The position of the carrier member 12 on the external thread of the externally threaded sleeve 11 can be altered by screwing it up to a greater or lesser extent and any setting that has been reached can be fixed by means of a locking nut 15 which is likewise screwed onto the external thread of the externally threaded sleeve 11 and can be screwed up against the carrier member 12 in the manner of a locking nut. The effective length of the component consisting of the externally threaded sleeve 11 on the one hand and the carrier member 12 with the support feet 13 on the other can thereby be altered and set. This component is mounted as a body on the housing 10 in longitudinally displaceable manner and is also protected from rotation about the rotational axis of the trepanning cutter 4 by means of a pin 17 engaging in an elongated slot 16.

A helical spring 19 surrounds the housing 10 on the one hand and the externally threaded sleeve 11 on the other and is supported at one end on the locking nut 15 and on an annular shoulder 18 of the housing 10 at the other end so that the component consisting of the externally threaded sleeve 11, the carrier member 12 and the support feet 13 will be moved into a starting position when the helical spring is untensioned, whereby in this position the support surfaces 14 completely cover the teeth 8 of the trepanning cutter 4 and these support surfaces 14 may possibly project slightly beyond the teeth 8.

The support feet 13 can be displaced towards the housing 10 against the action of the helical spring 19 thereby liberating the teeth 8. This displacement of the support feet 13 is limited by virtue of the upper edge 20 of the externally threaded sleeve 11 striking the annular shoulder 18 of the housing 10. This also defines how far the teeth 8 may project below the plane which is set by the support surface 14 and the support feet 13.

For the purposes of cutting out a cranial disc from a skull cap, the apparatus described is placed on the exterior of the cranial bone using the support surfaces 14 of the support feet 13 and then the drive appliance 1 is switched on so that the trepanning cutter 4 will rotate in oscillatory manner. The angle of rotation is thereby at least as great as the spacing between adjacent teeth so that cutting of the bone material in the region of the teeth may be effected over the whole periphery, namely in both directions of rotation.

The angle of rotation is chosen to be so low that any soft tissue that is carried along with the teeth will not be damaged by virtue of this movement.

During the cutting of the bone material, the operator presses the trepanning cutter 4 against the cranial bone whereby he compresses the helical spring 19 and pushes the trepanning cutter 4 against the effect thereof through the plane set by the support surface 14 of the support feet 13. The trepanning cutter 4 penetrates the cranial bone to the same extent and cuts out a central cranial disc from the cranial bone along an annular section line.

The maximum penetration depth is determined by the maximum displacement of the support feet 13 and, for its part, this maximum displacement can be set by virtue of the extent to which the carrier means 12 is screwed onto the external thread of the externally threaded sleeve 11.

In the embodiment of FIGS. 1 and 2, the trepanning cutter 4 achieves its support on the cranial bone by virtue of the outer support feet 13.

Such outer support feet 13 are also provided in the embodiment of FIG. 3, but the device in this embodiment in accordance with FIG. 3 is additionally provided with an inner support in the form of a central die 21 which can enter the cylindrical sleeve 5 of the trepanning cutter 4 from the open front end to a greater or lesser extent and thereby compress a helical spring 22 in the interior of the sleeve 5.

As illustrated in the embodiment of FIG. 3, the die 21 may be mounted in a special adapter 23 which is screwed into the sleeve of the trepanning cutter 4 whereby the depth to which the die 21 can be inserted can also be adjusted by virtue of the extent to which the adapter is screwed in.

The outer support feet 13 are supported on the outer edge of the opening that has been created whereas the die 21 is supported on the cranial disc at the centre of the opening.

Following the break-through, the cranial disc can be pressed into the interior of the skull in this manner and this leads to the soft tissue located therebelow being pushed inwardly over a large surface area and thus removed from the teeth 8 of the trepanning cutter 4, this thus acting as an additional protective measure for the soft tissue in the interior of the skull.

In addition, the die also simplifies the removal of the cranial disc which is disposed in the sleeve 5, this cranial disc being used after the operation has ended for closing the access point to the skull.

The present invention relates to the subject matter disclosed in German patent application 197 42 535.6 of Sep. 25, 1997, the entire specification of which is incorporated herein by reference.

What is claimed is:

1. A surgical instrument for cutting-out a cranial disc from the skull cap, comprising:
    a cylindrical trepanning cutter that widens toward a free end thereof into the form of a cylindrical sleeve provided with teeth on its frontal edge, which teeth cut in both peripheral directions;
    a driving means which drives the trepanning cutter with a periodically altering direction of rotation through an angle of rotation of substantially less than 360°, said angle being at least large enough for displacing the teeth by one tooth spacing along the frontal edge; and
    a support means associated with the trepanning cutter, which support means is displaceable along the rotational axis of the trepanning cutter between a starting position, in which the support means projects beyond the frontal edge, and an end position in which the support means liberates the frontal edge and a section of the trepanning cutter abutting thereon.

2. A surgical instrument in accordance with claim 1, wherein the support means is moved into the starting position by means of a spring.

3. A surgical instrument in accordance with claim 1, wherein a displacement path of the support means is limited at the end position by means of a stop.

4. A surgical instrument in accordance with claim 3, wherein the stop is adjustable in a direction along the displacement path of the support means.

5. A surgical instrument in accordance with claim 1, wherein the support means surrounds the trepanning cutter externally.

6. A surgical instrument in accordance with claim 5, wherein the support means comprises a plurality of mutually circumferentially displaced support feet.

7. A surgical instrument in accordance with claim 6, wherein the support feet delimit an open break-through area therebetween.

8. A surgical instrument in accordance with claim 6, wherein the support feet are mounted on a common carrier means that is displaceable in parallel with the rotational axis of the trepanning cutter.

9. A surgical instrument in accordance with claim 8, wherein the carrier means carries a stop limiting the displacement path of the support.

10. A surgical instrument in accordance with claim 9, wherein the carrier means is in the form of a ring which is screwed onto a thread on the stop which itself is in the form of a sleeve.

11. A surgical instrument in accordance with claim 10, wherein a helical spring supported on the ring surrounds the sleeve externally.

12. A surgical instrument in accordance with claim 10, wherein the sleeve forms a longitudinal guide means for the movement of the support means.

13. A surgical instrument in accordance with claim 1, wherein the support means is disposed internally of the trepanning cutter.

14. A surgical instrument in accordance with claim 13, wherein the support means comprises a spring-loaded die which is insertable into the trepanning cutter.

15. A surgical instrument in accordance with claim 1, wherein the trepanning cutter comprises openings in the wall thereof abutting onto the frontal edge.

16. A surgical instrument in accordance with claim 1, wherein the teeth on the outer surface of the trepanning cutter widen out radially towards the frontal edge.

17. A surgical instrument in accordance with claim 1, wherein the teeth on the inner surface of the trepanning cutter widen out radially towards the frontal edge.

* * * * *

UNITED STATES PATENT AND TRADEMARK OFFICE
CERTIFICATE OF CORRECTION

PATENT NO. : 6,129,731
DATED : October 10, 2000
INVENTOR(S) : Haeusler et al.

It is certified that error appears in the above-identified patent and that said Letters Patent is hereby corrected as shown below:

On the title page, item:

-- [30] Foreign Application Priority Data Sept. 25, 1997

[DE] Fed. Rep. of Germany ............... 197 42 535.7 --.

Signed and Sealed this

Eighth Day of May, 2001

NICHOLAS P. GODICI

Attest:

Attesting Officer

Acting Director of the United States Patent and Trademark Office